United States Patent
Nakajima et al.

(10) Patent No.: US 10,966,316 B2
(45) Date of Patent: Mar. 30, 2021

(54) WIRING FILM, DEVICE TRANSFER SHEET, AND TEXTILE TYPE DEVICE

(71) Applicant: JAPAN SCIENCE AND TECHNOLOGY AGENCY, Kawaguchi (JP)

(72) Inventors: Masao Nakajima, Tokyo (JP); Ichiro Amimori, Tokyo (JP); Osamu Sawanobori, Tokyo (JP); Takao Someya, Tokyo (JP)

(73) Assignee: JAPAN SCIENCE AND TECHNOLOGY AGENCY, Kawaguchi (JP)

( * ) Notice: Subject to any disclaimer, the term of this patent is extended or adjusted under 35 U.S.C. 154(b) by 0 days.

(21) Appl. No.: 15/767,227

(22) PCT Filed: Oct. 14, 2016

(86) PCT No.: PCT/JP2016/080530
§ 371 (c)(1),
(2) Date: Apr. 10, 2018

(87) PCT Pub. No.: WO2017/065272
PCT Pub. Date: Apr. 20, 2017

(65) Prior Publication Data
US 2019/0075652 A1   Mar. 7, 2019

(30) Foreign Application Priority Data
Oct. 16, 2015   (JP) .............................. JP2015-204500

(51) Int. Cl.
*H05K 1/03*   (2006.01)
*H05K 1/02*   (2006.01)
(Continued)

(52) U.S. Cl.
CPC ........... *H05K 1/038* (2013.01); *A61B 5/0205* (2013.01); *A61B 5/6805* (2013.01); *H01L 23/12* (2013.01);
(Continued)

(58) Field of Classification Search
CPC ............................ H05K 1/038; H05K 1/0353
(Continued)

(56) References Cited

U.S. PATENT DOCUMENTS 9,338,915 B1*   5/2016   Liu et al. .................. H05K 1/18
2002/0055313 A1*   5/2002   Velpari .................... C03C 25/10
                                                              442/180
(Continued)

FOREIGN PATENT DOCUMENTS

EP   3 100 677 A1   12/2016
JP   2006-332647 A   12/2006
(Continued)

OTHER PUBLICATIONS

International Search Report dated Jan. 10, 2017 in PCT/JP2016/080530 filed Oct. 14, 2016.
(Continued)

*Primary Examiner* — Binh B Tran
(74) *Attorney, Agent, or Firm* — Oblon, McClelland, Maier & Neustadt, L.L.P.

(57) ABSTRACT

A wiring film is provided between a cloth and an electronic component, wherein the wiring film has a wiring layer including an extensible film and wirings provided along the extensible film inside or on an outer surface of the extensible film and at least a part of the wirings is exposed from a first surface of the wiring layer that faces the electronic component.

13 Claims, 8 Drawing Sheets

(51) Int. Cl.
    *H01L 23/12*     (2006.01)
    *H01L 23/14*     (2006.01)
    *A61B 5/00*     (2006.01)
    *A61B 5/0205*     (2006.01)
    *H01L 23/13*     (2006.01)
    *A41D 1/00*     (2018.01)

(52) U.S. Cl.
    CPC .............. *H01L 23/13* (2013.01); *H01L 23/14* (2013.01); *H01L 23/145* (2013.01); *H05K 1/02* (2013.01); *H05K 1/0393* (2013.01); *A41D 1/005* (2013.01); *A61B 2562/164* (2013.01)

(58) Field of Classification Search
    USPC .......................... 361/749, 750, 760, 782, 783
    See application file for complete search history.

(56) References Cited

U.S. PATENT DOCUMENTS

| | | | |
|---|---|---|---|
| 2005/0235482 A1* | 10/2005 | Deaett et al. | H01P 11/00 29/600 |
| 2008/0090477 A1* | 4/2008 | Balthes et al. | B29C 43/003 442/136 |
| 2008/0204196 A1 | 8/2008 | Baba | |
| 2014/0299362 A1 | 10/2014 | Park et al. | |
| 2015/0181692 A1* | 6/2015 | Jezewski et al. | H05K 1/0393 361/679.03 |

FOREIGN PATENT DOCUMENTS

| | | | |
|---|---|---|---|
| JP | 2008-204345 A | 9/2008 |
| JP | 2011-47702 A | 3/2011 |
| JP | 2012-188799 A | 10/2012 |
| JP | 2014-25180 A | 2/2014 |
| WO | WO 2015/115441 A1 | 8/2015 |
| WO | WO 2015/138515 A1 | 9/2015 |

OTHER PUBLICATIONS

Extended European Search Report dated May 15, 2019 in Patent Application No. 16855525.8, citing documents AO-AQ and AX therein, 7 pages.

Rahimi, R. et al. "A sewing-enabled stitch-and-transfer method for robust, ultra-stretchable, conductive interconnects" Journal of Micromechanics and Microengineering, Institute of Physics Publishing, vol. 24, No. 9, XP020269417, 2014, 8 pages.

Office Action dated Sep. 15, 2020 in corresponding Japanese Patent Application No. 2017-545485 (with English Translation), citing document AA therein, 10 pages.

* cited by examiner

WIRING FILM, DEVICE TRANSFER SHEET, AND TEXTILE TYPE DEVICE

TECHNICAL FIELD

An embodiment of the present invention relates to a wiring film, a device transfer sheet, and a textile type device.

Priority is claimed on Japanese Patent Application No. 2015-204500, filed Oct. 16, 2015, the content of which is incorporated herein by reference.

BACKGROUND ART

In recent years, flexible electronics having various applications due to the softness of materials have attracted much attention. For example, attention has been paid to means for directly obtaining biological information such as movement of the human body by wearing flexible electronics on the surface of the human body or in the human body.

Patent Document 1 includes a strain-sensor-attached cloth including a strain sensor having a carbon nanotube film attached to a cloth and a wiring part connected to the strain sensor.

In addition, Patent Document 2 includes cloths in which a wiring part is integrally provided on a cloth main body. The wiring part is integrated with the cloth main body so that it becomes difficult for the wiring part to be cut and it is possible to minimize interference with a wearer's motion with the device.

CITATION LIST

Patent Literature

[Patent Document 1] Japanese Unexamined Patent Application, First Publication No. 2011-47702
[Patent Document 2] Japanese Unexamined Patent Application, First Publication No. 2014-25180

SUMMARY OF INVENTION

Technical Problem

The inventors studied sensor systems capable of measuring such motion or the like of the human body, and as a result, found many problems to be solved existing in the wirings for transmitting information from a sensor to an external output means.

In the strain-sensor-attached cloth described in Patent Document 1, one end of the wirings is connected to an electrode of the sensor but the other portion thereof is not fixed to a base member or the like. For this reason, when the number of wires increases, the wiring itself interferes with the wearer's hand motion or interferes with the wearer's movement.

In the strain-sensor-attached cloth described in Patent Document 2, the wiring part is directly formed on the cloth main body. Since a thread-like body having conductivity is knitted into the cloth, it cannot be said that conformability with respect to deformation or tension is sufficient. Furthermore, a short circuit between wirings may occur due to contact between wires, with sweat, or the like in some cases. Since the cloth is easily deformed even if it is attempted to adhere insulating layers to both surfaces of the wiring part to prevent a short circuit, it is difficult to position the insulating layers. In addition, there is a concern that impairment of stretchability or air permeability occurs due to the adhered insulating layers.

The present invention was made in view of the above circumstances, and an object of the present invention is to provide a textile type device in which there is less discomfort at the time of wearing the device and capable of minimizing occurrence of short circuits or the like. Furthermore, an object of the present invention is to provide a wiring pattern which can be suitably used for a device transfer sheet and a device transfer sheet which can be easily attached to a cloth in which the textile type device is deformed.

Solution to Problem

As a result of intensive studies, the inventors of the present invention found that a device transfer sheet having high flexibility can be obtained by forming wirings in a film having excellent stretchability. In addition, the inventors found that a textile type device in which there is less discomfort and which causes hardly any problems such as a short circuit at the time of wearing the device using the device transfer sheet can be obtained, thereby completing the present invention.

In other words, in order to accomplish the above objects, the present invention adopts the following means.

(1) A wiring film according to an embodiment of the present invention is a wiring film provided between a cloth and an electronic component, including: a wiring layer including an extensible film and wirings provided along the extensible film inside or on an outer surface of the extensible film, wherein at least a part of the wirings is exposed from a first surface of the wiring layer that faces the electronic component.

(2) In the wiring film according to (1), the wirings may be a conductive thread or a conductive thread coated with an insulating material.

(3) In the wiring film according to (1), the wirings may be a conductive wire or a conductive wire coated with an insulating material.

(4) In the wiring film according to any one of (1) to (3), the extensible film may include a polyurethane film.

(5) In the wiring film according to any one of (1) to (4), the extensible film may include a thermoplastic adhesive layer.

(6) In the wiring film according to any one of (1) to (4), the wiring film further includes: a short-circuit prevention layer on a second surface of the wiring layer opposite to the first surface.

(7) In the wiring film according to (6), the wiring film may be a polyurethane film including a thermoplastic adhesive layer on a first surface of the wiring layer in which the short-circuit prevention layer faces at least the cloth.

(8) A device transfer sheet according to an embodiment of the present invention includes: the wiring film according to any one of (1) to (7); an electronic component connected via an exposed portion of the wirings; a protective layer configured to cover the wiring film and the electronic component in a plan view; and a temporary support provided on a surface of the protective layer opposite to a surface thereof on the wiring film side.

(9) In the device transfer sheet according to (8), the electronic component may be a sensor.

(10) In the device transfer sheet according to (8) or (9), the protective layer and the wiring film may be provided only in a portion along the electronic component and wirings constituting the wiring film in the plan view.

(11) A textile type device according to an embodiment of the present invention includes: a cloth; the wiring film according to any one of (1) to (7) adhered on the cloth; an electronic component connected via an exposed portion of the wirings; and a protective layer configured to cover the wiring film and the electronic component in the plan view.

(12) In the textile type device according to (11), the protective layer and the wiring film may be provided only in the electronic component and the wirings constituting the wiring film in the plan view.

Advantageous Effects of Invention

A wiring film according to an embodiment of the present invention can be used as a wiring film for a device transfer sheet because the wiring film has adhesive properties and high stretchability.

In a device transfer sheet according to an embodiment of the present invention, an electronic component in which wirings are provided can be easily transferred to a cloth and a short circuit does not occur in the wirings.

A textile type device according to an embodiment of the present invention causes less discomfort and hardly any problems such as a short circuit at the time of wearing the device.

DESCRIPTION OF EMBODIMENTS

Figure 1:
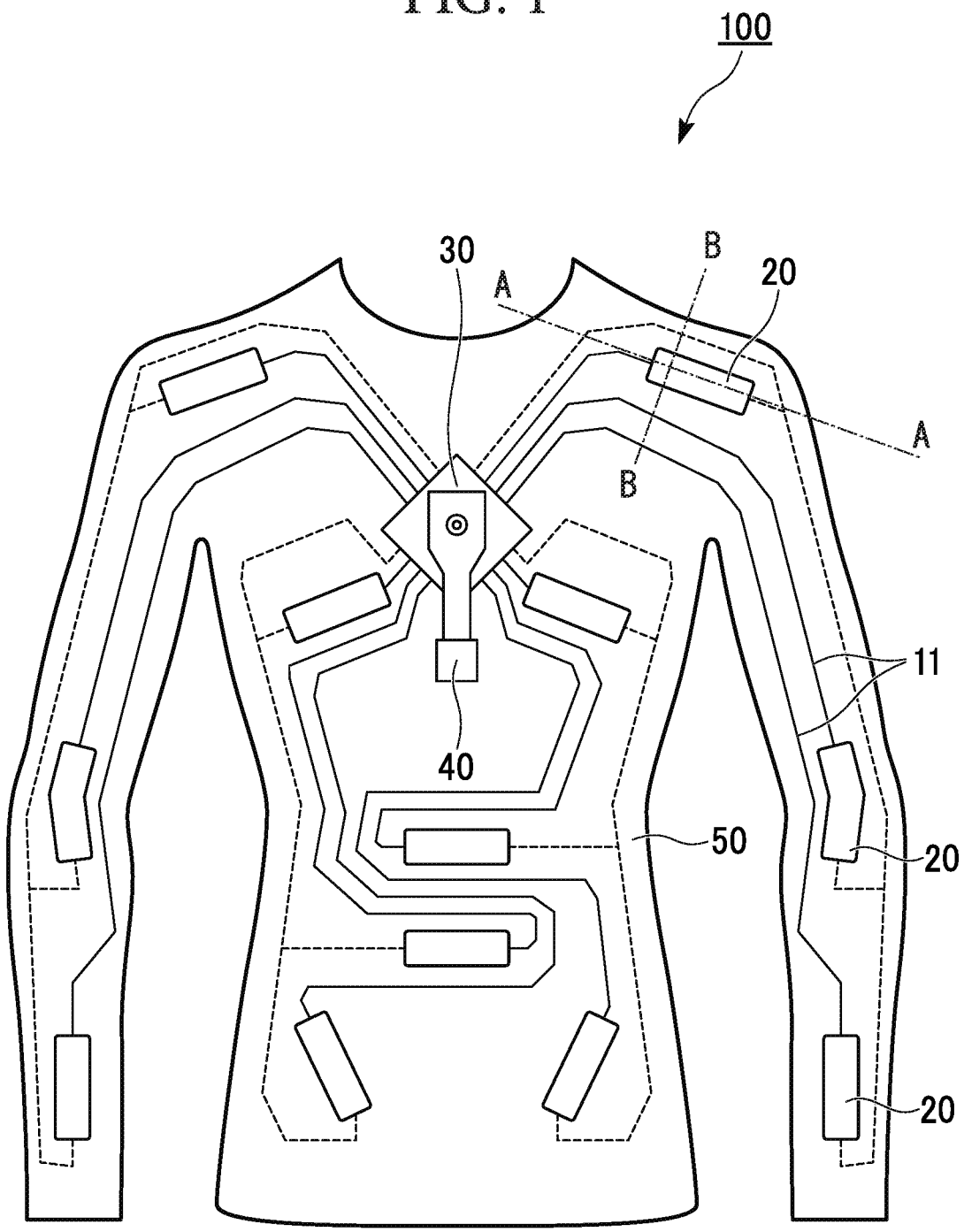
FIG. 1 is a schematic plan view of a textile type device according to an embodiment of the present invention.

Constituents including a wiring pattern, a device transfer sheet, and a textile type device to which the present invention is applied will be described below with reference to the drawings. In the drawings used in the following description, for the sake of facilitating understanding of the features, there are cases in which enlarged characteristic portions are shown for convenience and dimensional proportions of constituent elements are not necessarily the same as the actual ones. The materials, dimensions, and the like in the following description are merely exemplary examples, and the present invention is not limited thereto and can be appropriately modified and implemented without departing from the gist of the present invention.

(Textile Type Device and Wiring Film)

FIG. 1 is a schematic plan view of a textile type device according to an embodiment of the present invention.

A textile type device 100 includes a cloth 50, a plurality of electronic components (sensors) 20 provided in the cloth 50, a circuit board 30 in which information from the sensors 20 is integrated, an external output means 40 for outputting the information integrated in the circuit board 30 to the outside, and wirings 11 configured to connect the sensors 20 and the circuit board 30.

Figure 2:
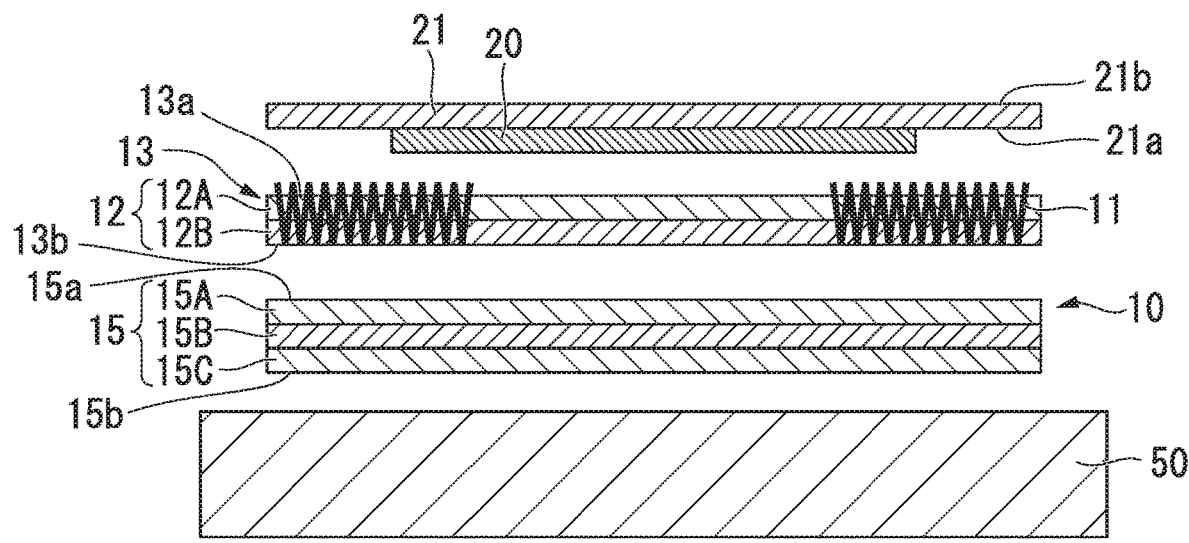
FIG. 2 is a cross-sectional view schematically showing an example of a cross section of a textile type device shown in FIG. 1 taken along surface A-A.

FIG. 2 is a cross-sectional view schematically showing an example of a cross section of the textile type device shown in FIG. 1 taken along surface A-A. As shown in FIG. 2, the wirings 11 are provided in a wiring film 10. The wiring film 10 is disposed between the cloth 50 and one of the sensors 20 and a protective layer 21. A wiring layer 13 and an adhesive layer 15 constituting the wiring film 10, the sensor 20, the protective layer 21, and the cloth 50 are actually in contact with each other, but are shown by being partially separated for the sake of helping understanding thereof.

The wiring film 10 shown in FIG. 2 includes the wiring layer 13 and a short-circuit prevention layer 15.

The wiring layer 13 includes an extensible film 12 and a wirings 11 provided along the extensible film 12 inside or on an outer surface of the extensible film 12.

A part of the wirings 11 is exposed from at least a first surface 13a of the wiring layer 13 on the sensor 20 side. The part of the wirings 11 is exposed from the first surface 13a so that the wiring 11 can be in contact with the sensor 20.

In the wiring film of the present invention, in order to bring the wirings into contact with the sensor while securing insulation of the wirings, only a part of the wirings may be exposed from the first surface. In this case, the wirings are provided inside and on the outer surface of the extensible film.

As the wirings 11, stretchable wiring such as a conductive thread, a conductive wire, a conductive ink, or the like can be used. In the specification, a "conductive thread" refers to a natural fiber or a chemical fiber coated with a conductive material and a "conductive wire" refers to a wire-like member made of a conductive material. The conductive wire is typically a metallic wire, but is not limited to a metallic wire as long as the conductive wire has conductivity. Particularly, it is desirable to use a conductive thread or a conductive wire for the wirings 11 and it is more desirable to use a conductive thread coated with silver and a copper wire as the conductive thread and the conductive wire, respectively. The conductive thread is a thread having conductivity. The conductive thread has high durability and high conformability to changes in shape. For this reason, deformation or the like of the textile type device 100 can also be prevented using a conductive thread. A copper wire has high conductivity and low variation in resistance. As an application thereof, for example, conductive threads are used for wirings between sensors like in conventional motion capture and copper wires may be used for wirings of a digital device (in which high conductivity is required) for the purpose of adding further functions.

The wirings 11 may be used by being coated with an insulating material. In this case, a portion exposed from the first surface of the wiring layer facing the electronic component is not coated with an insulating material.

It is desirable that the wirings 11 meander. A meandering shape can be any shape such as a zigzag, a waveform, a curve obtained by aligning a plurality of horseshoe shapes and/or parts of horseshoe shapes and joining or interpolating between ends thereof, a continuous hairpin curve, a line obtained by combining a plurality of parts of polygons, and a line obtained by combining a plurality of parts of star shapes, or combinations thereof, a substantially straight line and an approximate curve, and combinations of a substantially straight line and an approximate curve.

A period of meandering and a width of meanders can have any values. Furthermore, meanders may not have the same shapes, the same period, and/or width and may have different values. When the wirings 11 such as the conductive thread or the conductive wire meander, conformability to the deformation of the extensible film 12 can be improved.

Any member having stretchability can be used for the extensible film 12. Since the extensible film 12 stretches and contracts, a textile type device 100 which can conform to deformation such as stretching and bending can be obtained. Here, in the case of stretchability, an amount of change in shape with respect to an initial state is preferably 30% or more, more preferably 50% or more, and particularly preferably 100% or more.

Although a thickness of the extensible film 12 is not particularly limited, the thickness thereof is preferably 5 µm to 300 µm and more preferably 10 µm to 100 µm. Both high stretchability and strength can be achieved as long as the thickness of the extensible film 12 is in this range.

In FIG. 2, the extensible film 12 is constituted of an adhesive layer 12A and an insulating layer 12B from the first surface side of the extensible film. When the adhesive layer 12A is thermally melted, the wiring film 10, the sensor 20, and the protective layer 21 can be fused and joined. As the insulating layer 12B, any member having stretchability such as a polyurethane film can be used. The adhesive layer 12A is preferably a thermoplastic adhesive layer and examples of thermoplastic adhesive layer include known hot melt films and the like, but it is desirable that the adhesive layer 12A be a hot melt film having stretchability.

Thus, conformability at the time of the cloth stretching and contracting is improved. Examples of a hot melt having stretchability include a hot melt film or the like having polyurethane as a main ingredient.

A conductive hot melt containing conductive metal particles may be partially used between contact points of the sensor 20 and the wirings 11. Thus, an electrical connection between the sensor 20 and the wirings 11 can be improved so that contact resistance is reduced. As conductive metallic fine particles used for the conductive hot melt, silver, gold, copper, platinum, or aluminum is preferable, silver, gold, or copper is more preferable, and silver is most preferable. Furthermore, using flake-like metallic fine particles, high conductivity can be imparted with a small content. It is desirable that the conductive hot melt include a hot melt having polyurethane as a main ingredient. Thus, detaching from the sensor 20 or the wirings 11 due to distortion applied at the time of the cloth stretching and contracting can be minimized.

The extensible film 12 is not limited to this embodiment. For example, the extensible film 12 may be constituted only of the insulating layer 12B made of a polyurethane film, adhesive layers may be formed on both surfaces of the insulating layer 12B, and the extensible film 12 may be constituted only of an adhesive layer. Modifications thereof will be described below in detail.

The short-circuit prevention layer 15 is disposed on a second surface 13b of the wiring layer 13 opposite to the first surface 13a. In the wiring layer 13, if the wirings 11 are not exposed from the second surface 13b, the short-circuit prevention layer 15 may be omitted. However, as the short-circuit prevention layer 15 is provided on the second surface 13b of the wiring layer 13, a short circuit due to penetration of sweat or the like from the cloth 50 can be more effectively prevented. The present invention can also be used underwater or the like.

The short-circuit prevention layer 15 also has a function of adhering the wiring layer 13 to the cloth 50. The textile type device 100 functions as a wearable device. For this reason, it is assumed that washing or the like is performed. Since the short-circuit prevention layer 15 firmly adheres the wiring layer 13 to the cloth 50, detaching of the short-circuit prevention layer 15 can be prevented when treatment using water such as washing is performed.

It is desirable that the short-circuit prevention layer 15 have the first surface 15a thereof on the wiring layer 13 side and a second surface 15b thereof opposite to the first surface 15a and have at least an adhesive layer 15C on the second surface 15b.

In FIG. 2, an example in which an adhesive layer 15A and the adhesive layer 15C are provided on both surfaces of an insulating layer 15B is shown.

It is desirable that thermoplastic adhesive layers be used for the adhesive layers 15A and 15C. Thus, conformability at the time of the cloth stretching and contracting can be improved and the wiring layer 13 and the cloth 50 are firmly adhered. Examples of thermoplastic adhesive layer include a known hot melt film or the like, but it is desirably a hot melt film having stretchability. Examples of a hot melt having stretchability include a hot melt or the like having polyurethane as a main ingredient.

Also, as the short-circuit prevention layer 15 includes the insulating layer 15B, the short-circuit prevention layer 15 can embed the wirings 11 exposed from the second surface 13b of the wiring layer 13 on the cloth 50 side, thereby further improving insulating properties. Thus, short circuiting of the textile type device due to sweat or the like can be minimized. Furthermore, as the short-circuit prevention layer 15 is provided, the strength of the entire wiring film 10 can be further increased. It is desirable to use a polyurethane film as the insulating layer 15B. Thus, high insulation properties can be ensured and conformability at the time of the cloth stretching and contracting is improved.

A thickness of the short-circuit prevention layer 15 is not particularly limited, but is preferably 10 µm to 800 µm and more preferably 30 µm to 300 µm. Regarding each of the constituents of the short-circuit prevention layer 15, a thickness of the insulating layer 15B is preferably 5 µm to 300 µm and more preferably 10 µm to 100 µm. High stretchability and strength can be maintained as long as the thickness of the insulating layer 15B is in this range. Thicknesses of the adhesive layers 15A and 15C are preferably 10 µm to 200 µm and more preferably 30 µm to 100 µm. When the thickness of the adhesive layer 15C is within this range, the cloth and the wiring film 10 can be strongly adhered to each other and can be used for a long period of time without becoming detached due to washing or the like.

The wiring film 10 constituted of the wiring layer 13 and the short-circuit prevention layer 15 preferably has a conductivity when a shape thereof has changed by 10% or more that is 1/10 to 10 times a conductivity when the shape thereof has not changed. Furthermore, it is desirable that a proportion of conductivity change be kept in this range even if the shape thereof changes by 30% or more, it is more desirable that the proportion of conductivity change be kept in this range even if the shape thereof changes by 50% or more, and it is particularly desirable that the proportion of conductivity change be kept in this range even if the shape thereof changes by 100% or more.

A short-circuit prevention layer 15 is not limited to this example and various constitutions thereof can be adopted. For example, the short-circuit prevention layer may also serve as a thermoplastic adhesive layer. Furthermore, the short-circuit prevention layer 15 may be constituted of a more plurality of layers.

Examples of the sensor 20 include a photodiode, a temperature sensor, a strain sensor, a pressure sensor, and the like. In addition, different sensors may be used for different places. Depending on usage applications, the sensor 20 may be replaced with an electronic component other than a sensor.

The sensor 20 is not particularly limited as long as a current or a voltage of the sensor changes due to a change in a physical quantity, but is preferably a variable resistance type sensor whose resistance varies depending on a physical quantity and a voltage of which at both ends changes, due to the simplicity or the like of a circuit. As the physical quantity, at least one of the group consisting of sound, light, temperature, pressure, and strain can be suitably used. In this case, a resistance value of the resistance of the sensor 20 is preferably 50 times or more a wiring resistance of the wirings 11. A distance between the sensor 20 and an external output means 5 differs depending on a location, but the resistance of the sensor 20 is set to a value that is 50 times or more the wiring resistance so that an influence of the wiring resistance of the wirings 11 can be eliminated.

In the case of the sensor 20, it is desirable to use a sensor using ink. A sensor using ink is a sensor prepared using ink obtained by mixing conductive particles with an elastomer solution or a dispersion. By printing and drying this ink, a sensor in which the conductive particles are randomly dispersed in an elastomer film is obtained. In the sensor, distances between conductive particles change in accordance with thermal expansion/contraction due to tension, compression, and change in temperature and thus the resistance between both ends of the sensor changes. A sensor using ink is very thin and conformability to an object on which measurement is to be performed is high. For this reason, accurate and stable measurement can be performed.

As shown in FIG. 2, the protective layer 21 covers the wiring film 10 and the sensor 20 in a plan view. A surface 21b of the protective layer 21 on a side opposite to a surface 21a on which the sensor 20 is provided is an outermost surface in a state of being used. In other words, the wiring film 10 and the sensor 20 are covered with the protective layer 21 so that the wirings 11 can be embedded in a device transfer sheet 100.

As a result, the wiring film 10 can be protected from erosion due to sweat or the like when a textile type device obtained using the device transfer sheet 100 is used. The textile type device can also be used underwater.

The protective layer 21 is the outermost surface when the textile type device is used as described above. For this reason, it is desirable that the protective layer 21 have insulating properties and stretchability. In addition, it is desirable that the protective layer 21 be a layer made of polyurethane.

A thickness of the protective layer 21 is preferably 5 µm to 300 µm and more preferably 10 µm to 100 µm. High stretchability and strength can be maintained as long as the thickness of the protective layer 21 is in this range.

Figure 3:
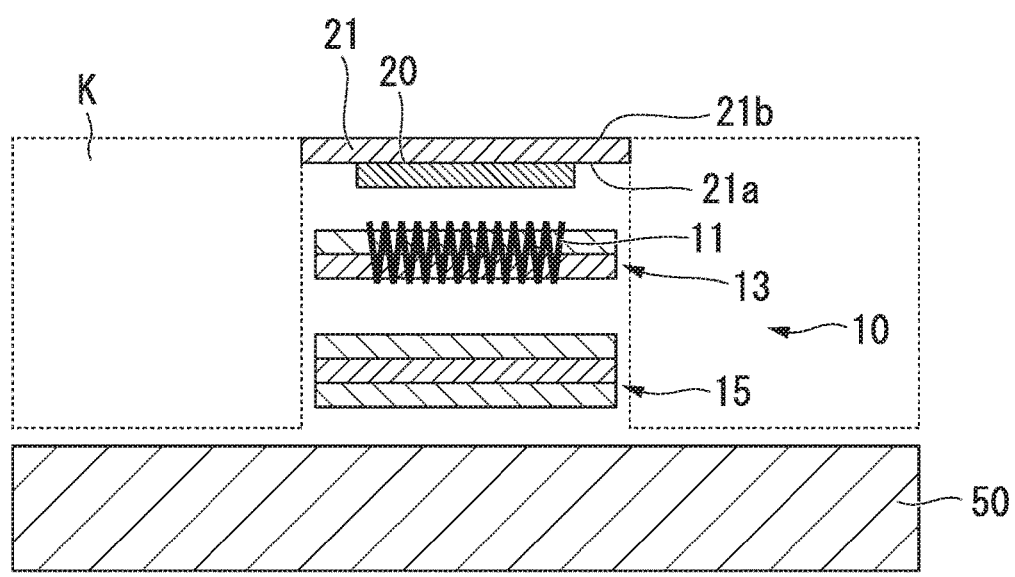
FIG. 3 is a cross-sectional view schematically showing an example of a cross section of the textile type device shown in FIG. 1 taken along surface B-B.

FIG. 3 is a cross-sectional view schematically showing an example of a cross section of the textile type device shown in FIG. 1 taken along surface B-B.

As shown in FIG. 3, it is desirable that the protective layer 21 and the wiring film 10 (wiring layer 13 and short-circuit prevention layer 15) be provided only in a portion along the wirings 11 constituting the sensor 20 and the wiring film 10 in a plan view. The protective layer 21 and the wiring film 10 are provided only in a necessary minimum portion along the wirings 11 in this way so that a space K to which nothing is attached is formed above the cloth 50. Due to the presence of the space K, air permeability and flexibility of the textile type device 100 can be further improved.

Here, the portions along the sensor 20 and the wirings 11 are preferably in a range of 0.1 mm to 100 mm from outer peripheries of the sensor 20 and the wirings 11 in a plan view and more preferably 0.5 mm to 5 mm. If the portions along the sensor 20 and the wirings 11 are too large, there are more unnecessary portions and thus air permeability of the textile type device is hindered. On the other hand, if the portions along the sensor 20 and the wirings 11 are too narrow, a part of the sensor 20 and the wirings 11 is highly likely to be exposed to the outside due to a level difference between the sensor 20 and the wirings 11 and a short circuit is highly likely to occur.

Various cloths can be used as the cloth 50. For example, existing cloths may be used as the cloth 50. Since a sensitivity of the sensor 20 can be increased when the sensor 20 is in close contact with a person, it is desirable that the cloth 50 be made of a stretchable material.

The circuit board 30 is a part configured to collect information from sensors attached to various portions.

As the circuit board 30, known boards can be used. For example, a flexible printed circuit board or the like can be used.

The external output means 40 is a part configured to output electrical information from the sensor 20 to the outside.

The external output means 40 may be a wired communication device or a wireless communication device as long as the external output means 40 can transmit a signal to the outside. From the viewpoint of reducing discomfort at the time of wearing, it is desirably a wireless communication device. For example, a communication standard such as Bluetooth (registered trademark), Zigbee (registered trademark), and Wi-Fi (registered trademark) can be used. A microcomputer, a lithium battery, and the like may also be installed in the external output means.

MODIFICATIONS

Note that description has been provided with reference to FIGS. 1 to 3, but the textile type device is not necessarily limited to this constitution and various modifications are possible without departing from the gist of the present invention.

Figure 4:
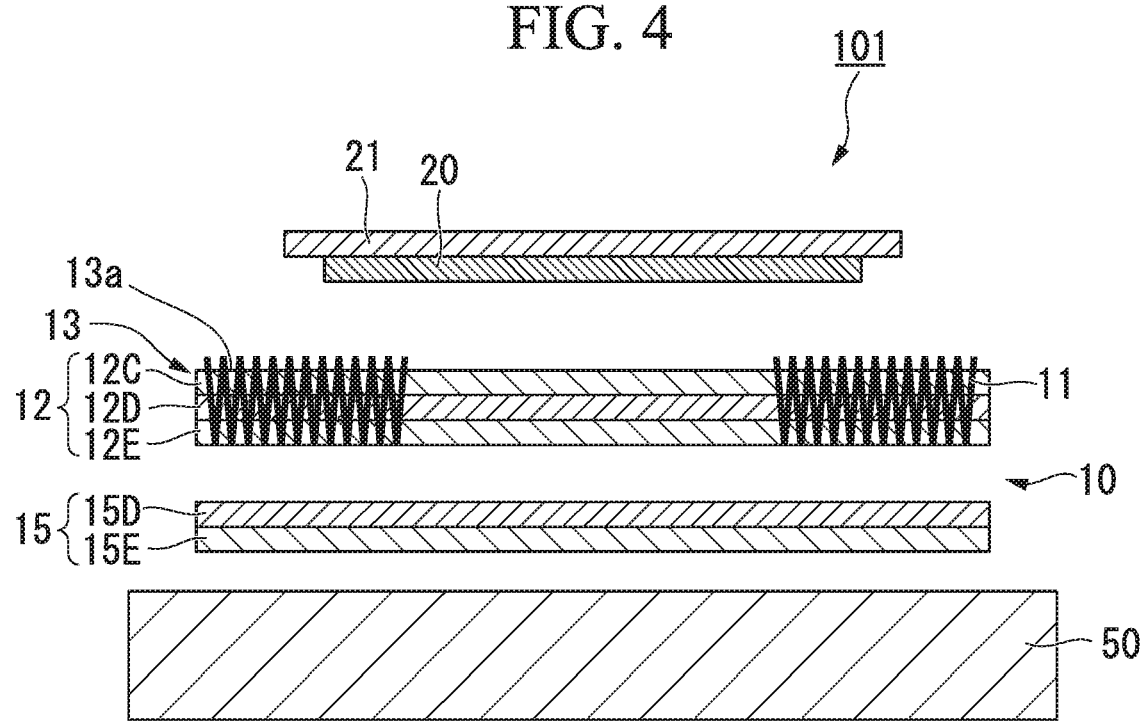
FIG. 4 is a cross-sectional view schematically showing another example of a cross section of the textile type device shown in FIG. 1 taken along surface A-A.

FIG. 4 shows a modification and is a cross-sectional view corresponding to a cross section of the textile type device shown in FIG. 1 taken along surface A-A. In a textile type device 101 shown in FIG. 4, a wiring layer 12 and a short-circuit prevention layer 15 constituting a wiring film 10 have different constitutions. Other constituents are the same as those of the above-described textile type device 100 and are denoted with the same reference numerals.

In the textile type device 101, an extensible film 12 has three layers and the short-circuit prevention layer 15 has two layers. The extensible film 12 is constituted of an insulating layer 12B having adhesive layers 12C and 12F on both surfaces thereof. The short-circuit prevention layer 15 is constituted of an insulating layer 15D having an adhesive layer 15E on a surface thereof on a cloth 50 side. When the constitution of the textile type device 100 shown in FIG. 2 is compared with the constitution of the textile type device 101 shown in FIG. 4, the overall thickness thereof has not changed but the extensible film is thicker. For this reason, an effect in which the extensible film is difficult to damage when a conductive thread wirings are formed is achieved.

Also in the textile type device 101, since a part of the wirings 11 is exposed from a first surface 13a of a wiring layer 13, application of electricity to the sensor 20 can be secured. Since the short-circuit prevention layer 15 is arranged on a portion of the wiring layer 13 on the cloth 50 side, penetration of sweat or the like from the cloth 50 can be prevented. In other words, a short circuit caused by sweat or the like can be prevented.

Figure 5:
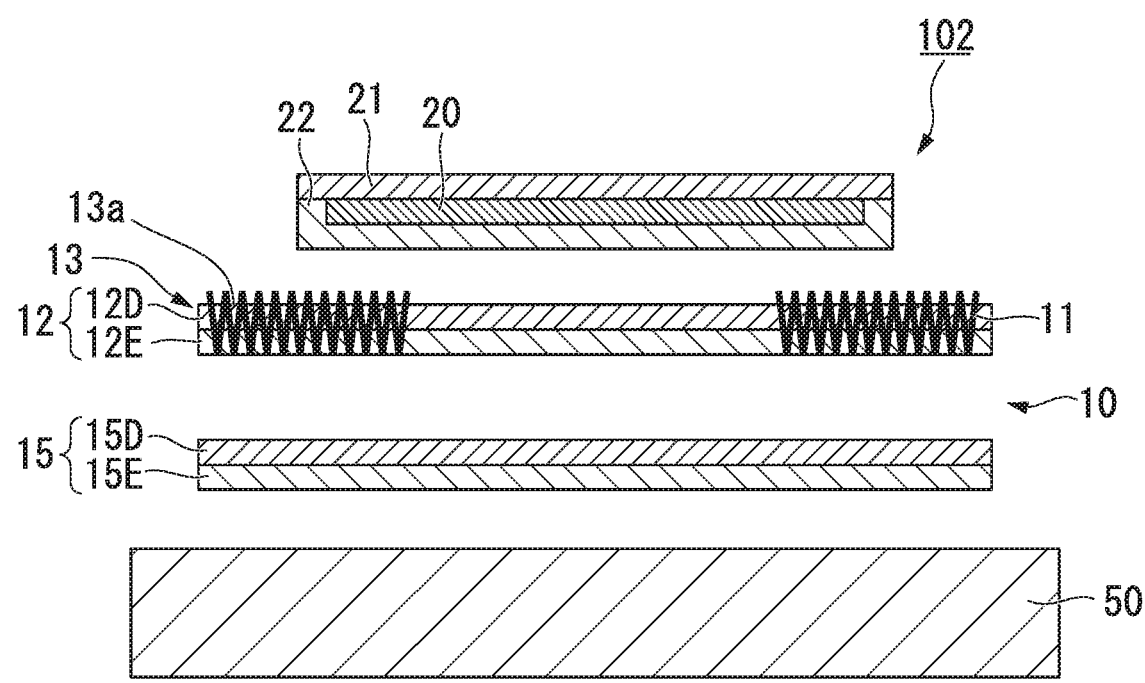
FIG. 5 is a cross-sectional view schematically showing yet another example of a cross section of the textile type device shown in FIG. 1 taken along surface A-A.

Also, FIG. 5 shows another modification and is a cross-sectional view corresponding to a cross section of the textile type device shown in FIG. 1 taken along surface A-A. A textile type device 102 shown in FIG. 5 and the above-described textile type device 101 differ in that, in the textile type device 102, an adhesive layer 22 having the same function as that of the adhesive layer 12C of the wiring layer 13 in the above-described textile type device 101 arranged on the sensor 20 side is arranged on the sensor 20 and protective layer 21 sides. Other constituents are the same as those of the above-described textile type device 100 and denoted with the same reference numerals.

In the textile type device 102, there in a concern concerning interference with connection between the sensor 20 and wirings 11 due to an adhesive layer 22. However, connection is possible without any problem as long as the adhesive layer 22 can be sufficiently melted by heat or the like at the time of adhering. In other words, also in the textile type device 102, application of electricity to the wirings 11 and the sensor 20 can be secured and penetration of sweat or the like from a cloth 50 can be prevented. In other words, a short circuit caused by sweat or the like can be prevented.

Figure 6:
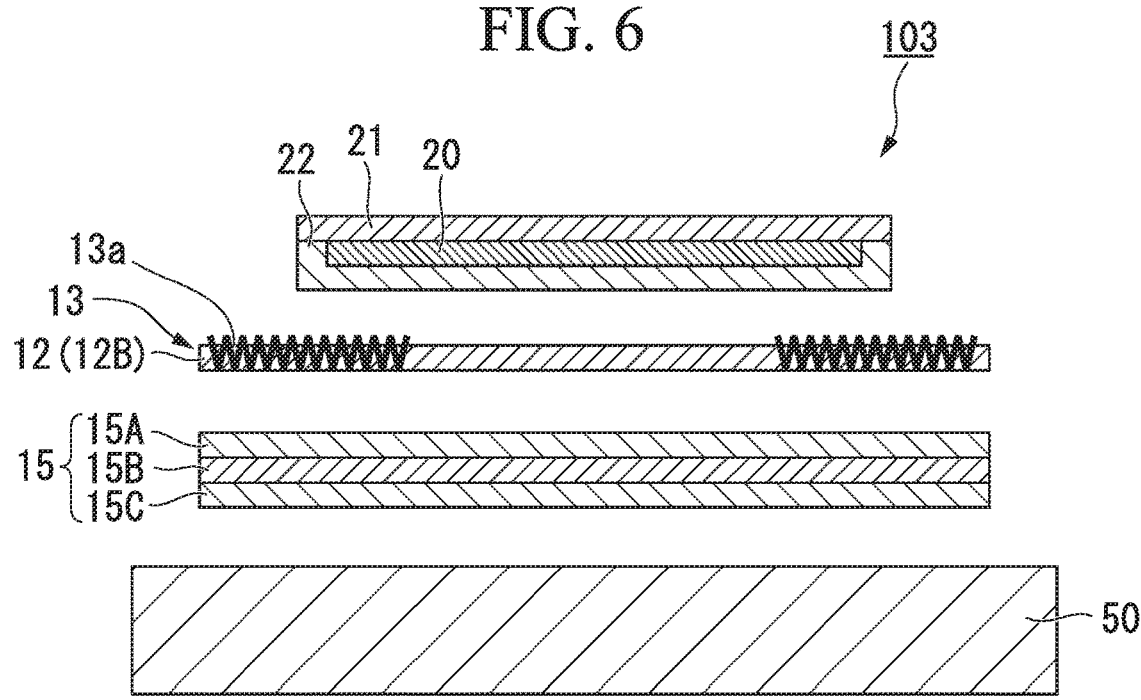
FIG. 6 is a cross-sectional view schematically showing still another example of a cross section of the textile type device shown in FIG. 1 taken along surface A-A.

FIG. 6 shows yet another modification and is a cross-sectional view corresponding to a cross section of the textile type device shown in FIG. 1 taken along surface A-A. A textile type device 103 shown in FIG. 6 and the above-described textile type device 100 differ in that, in the textile type device 103, an adhesive layer 22 having the same function as that of the adhesive layer 12A of the wiring layer 13 in the textile type device 100 arranged on the sensor 20 side is arranged on the sensor 20 and protective layer 21 sides. Other constituents are the same as those of the above-described textile type device 100 and denoted with the same reference numerals.

Also in the textile type device 103, there is a concern about interference with connection between the sensor 20 and wirings 11 due to an adhesive layer 22. However, connection is possible without any problem as long as the adhesive layer 22 can be sufficiently melted by heat or the like at the time of adhering. In other words, also in the textile type device 103, application of electricity to the wirings 11 and the sensor 20 can be secured and penetration of sweat or the like from the cloth 50 can be prevented. In other words, a short circuit caused by sweat or the like can be prevented.

Figure 7:
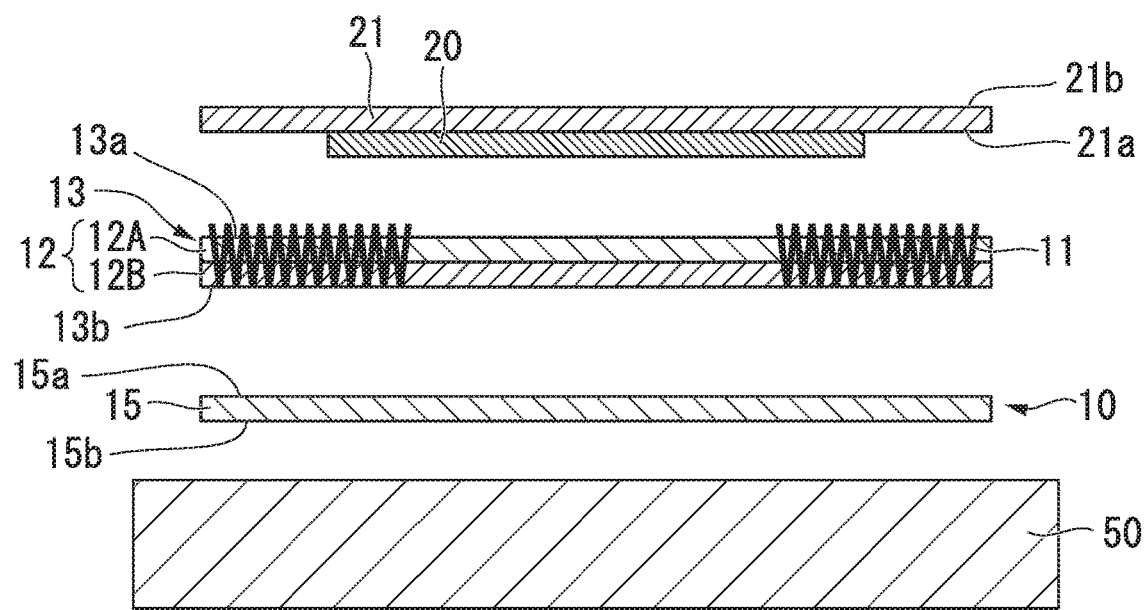
FIG. 7 is a cross-sectional view schematically showing still another example of a cross section of the textile type device shown in FIG. 1 taken along surface A-A.
Figure 8:
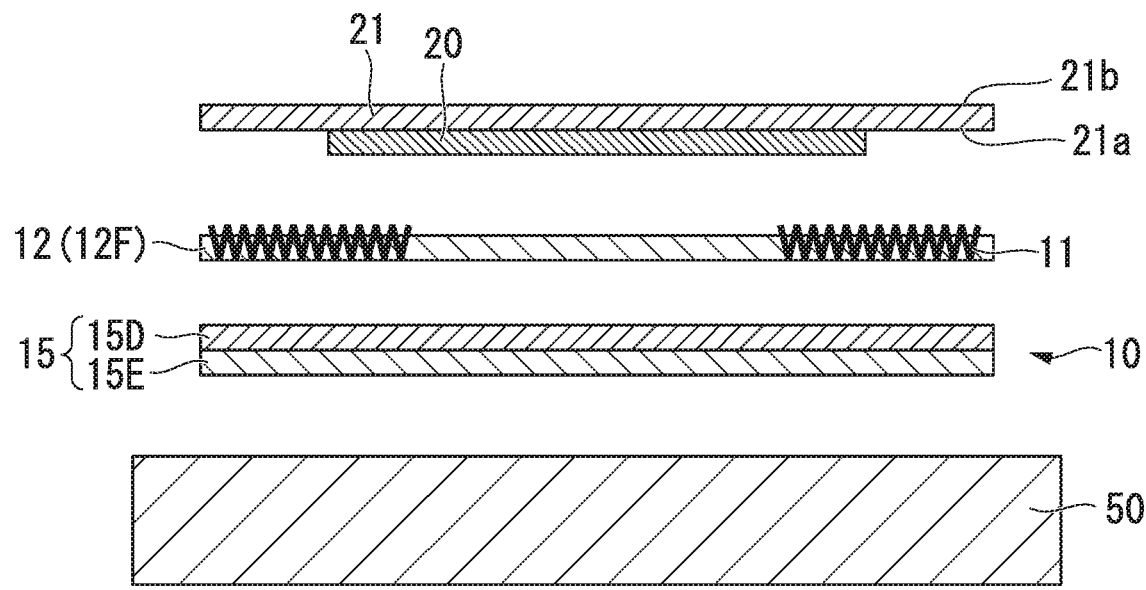
FIG. 8 is a cross-sectional view schematically showing still another example of a cross section of the textile type device shown in FIG. 1 taken along surface A-A.
Figure 9:
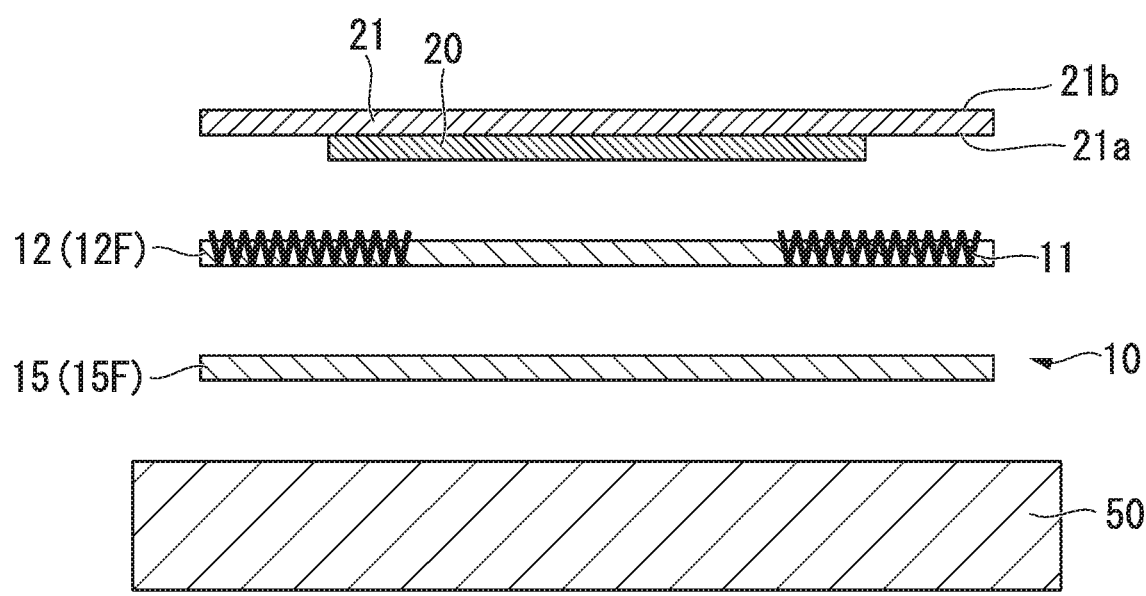
FIG. 9 is a cross-sectional view schematically showing still another example of a cross section of the textile type device shown in FIG. 1 taken along surface A-A.
Figure 10:
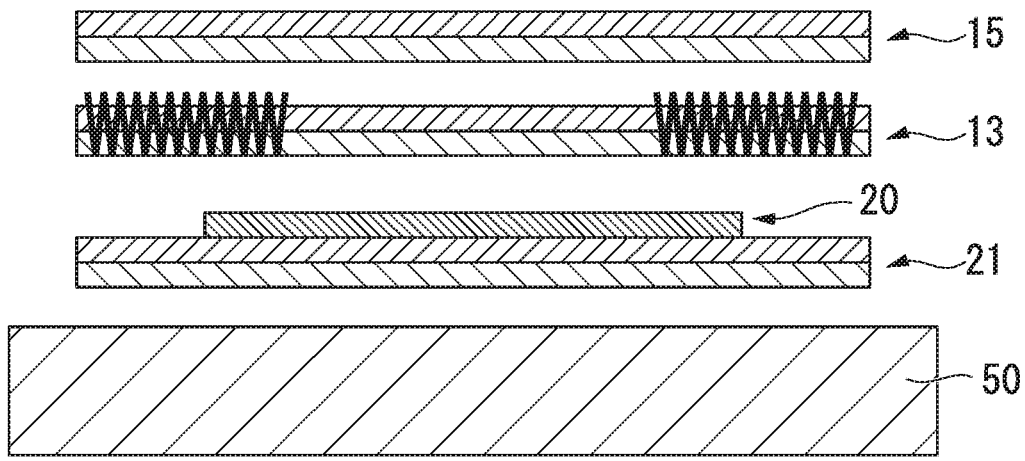
FIG. 10 is a cross-sectional view schematically showing still another example of a cross section of the textile type device shown in FIG. 1 taken along surface A-A.
Figure 11:
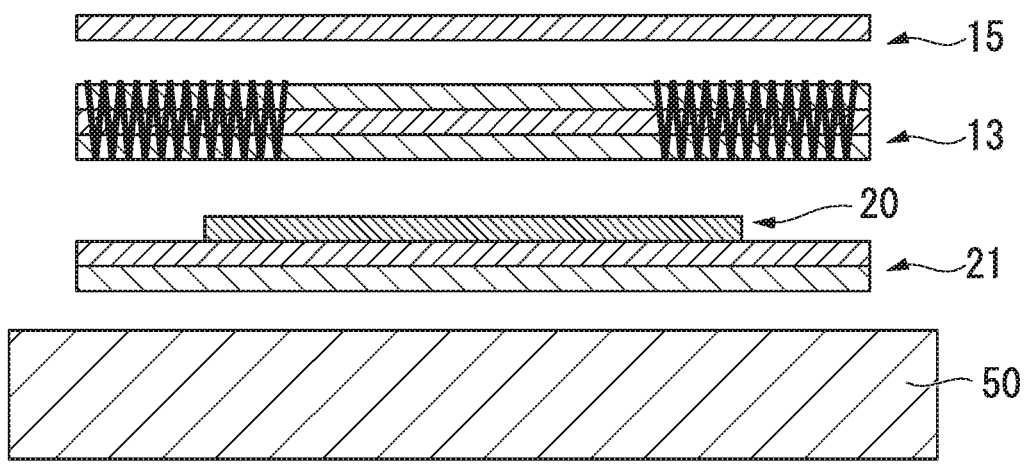
FIG. 11 is a cross-sectional view schematically showing still another example of a cross section of the textile type device shown in FIG. 1 taken along surface A-A.
Figure 12:
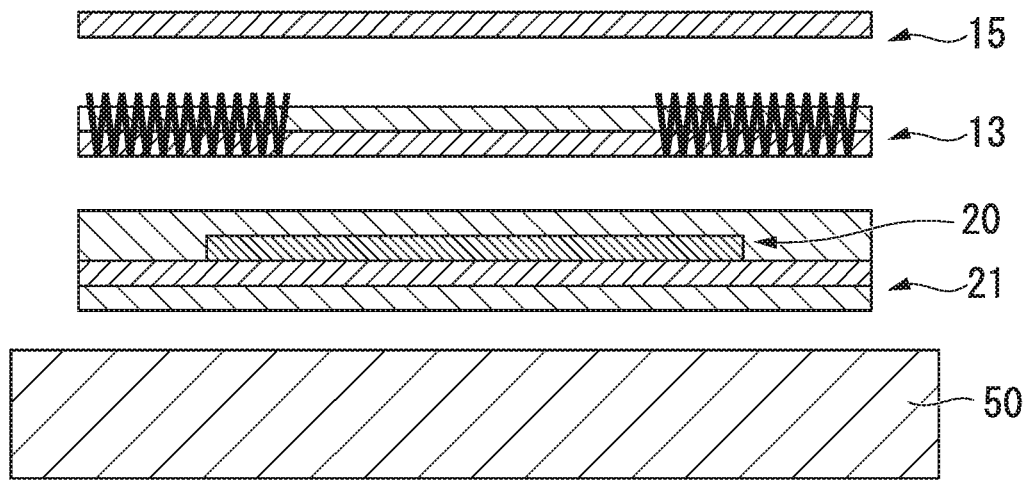
FIG. 12 is a cross-sectional view schematically showing still another example of a cross section of the textile type device shown in FIG. 1 taken along surface A-A.
Figure 13:
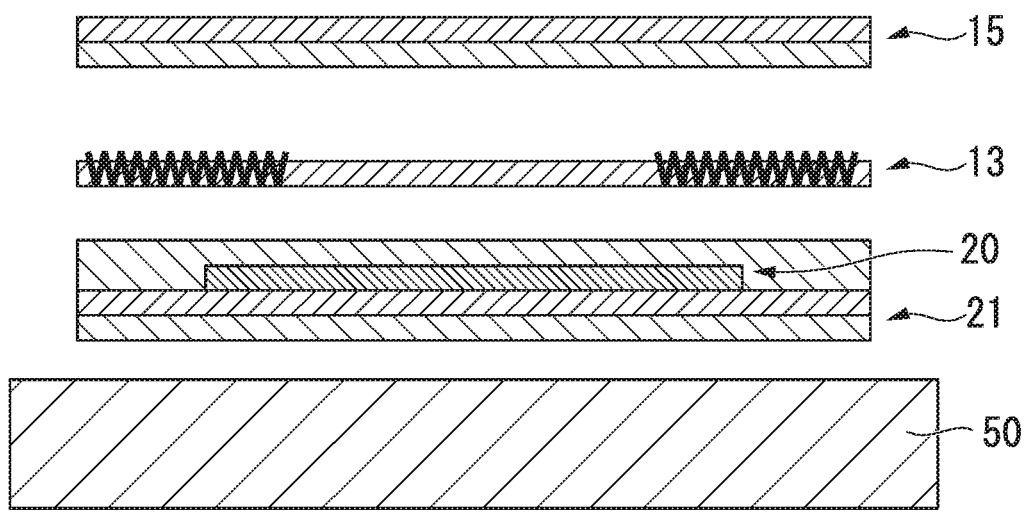
FIG. 13 is a cross-sectional view schematically showing still another example of a cross section of the textile type device shown in FIG. 1 taken along surface A-A.

Besides this, various embodiments can be used as long as adhesion among the protective layer 21, the sensor 20, a wiring layer 13, a short-circuit prevention layer 15, and a cloth 50 can be maintained and the wirings 11 can be embedded therein. For example, the short-circuit prevention layer 15 may include only one layer of adhesive layer 15F as shown in FIGS. 7 and 9 and the extensible film 12 may include only one layer of an adhesive layer 12F as shown in FIGS. 8 and 9. Furthermore, as shown in FIGS. 10 to 13, an order of the sensor 20, the wiring layer 13, and the short-circuit prevention layer 15 with respect to the cloth 50 may be reversed. To be specific, the cloth 50, the sensor 20, the wiring layer 13, and the short-circuit prevention layer 15 may be stacked in this order.

As described above, the textile type device according to the embodiment of the present invention is used so that a wearable sensor device can be obtained. Furthermore, short circuiting caused by moisture such as sweat, discomfort due to poor air permeability, and the like can be prevented, thereby allowing a device with less discomfort to the wearer to be provided.

"Device Transfer Sheet"

Figure 14:
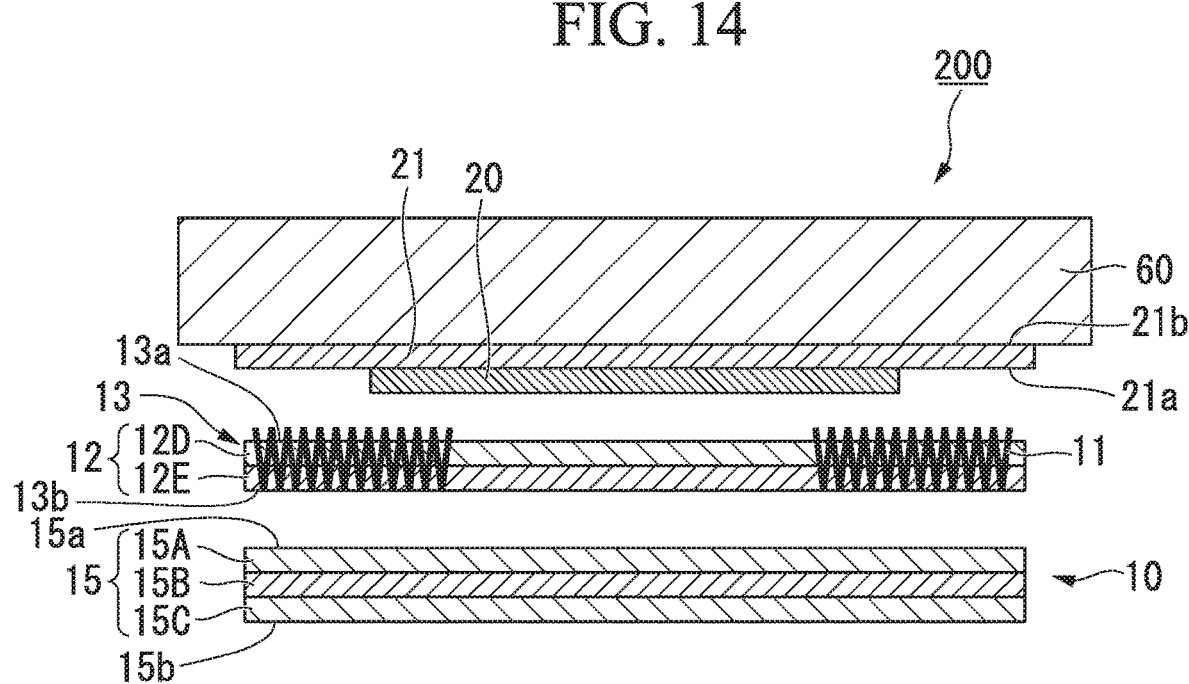
FIG. 14 is a schematic cross-sectional view of a device transfer sheet according to an embodiment of the present invention.

FIG. 14 is a schematic cross-sectional view of a device transfer sheet according to an embodiment of the present invention. A device transfer sheet 200 according to the embodiment of the present invention includes a wiring film 10, a sensor 20, a protective layer 21, and a temporary support 60.

When the device transfer sheet 200 is transferred to a cloth and the temporary support 60 is detached, the device transfer sheet 200 functions as a textile type device of the present invention like the textile type device 100 to 103 described above. An example shown in FIG. 14 is a case in which the textile type device 100 is provided, the wiring film 10, the sensor 20, and the protective layer 21 have the same constituents as those of the textile type device 100, and detailed description thereof will be omitted.

The temporary support 60 is a support part configured to support the wiring film 10, the sensor 20, and the protective layer 21 until the textile type device is transferred to the cloth. The temporary support 60 is detached when the textile type device is used. For this reason, a material of the temporary support 60 is not particularly limited. For example, a commercially available polyethylene terephthalate (PET) film or the like can be used.

A thickness of the temporary support 60 is preferably 20 µm or more, more preferably 50 µm or more, and particularly preferably 100 µm or more. If the thickness of the temporary support 60 is in this range, the wiring film 10, the sensor 20, and the protective layer 21 can be sufficiently supported. On the other hand, if the thickness of the temporary support 60 is too thick, there is a problem that the manufacturing costs of the entire device transfer sheet 200 increase and a thickness and weight thereof unnecessarily increase.

As described above, it is desirable to remove unnecessary portions other than the wirings 11 and the sensor 20 from the viewpoint of ensuring air permeability of the textile type device, reducing the weight thereof, improving flexibility thereof, and the like. In other words, it is desirable to remove the protective layer 21 and the wiring film 10 other than portions along the wirings 11 and the sensor. When the protective layer 21 and the wiring film 10 are removed, it is desirable that the unnecessary portions be cut in half without cutting the temporary support 60. If the temporary support 60 is also removed together therewith, it becomes difficult for the device transfer sheet 200 to maintain its shape and thus handling properties significantly deteriorate. For this reason, a transfer accuracy or the like to the cloth deteriorates. On the other hand, when the unnecessary portions are cut in half while the temporary support 60 is left, transfer of the device transfer sheet 200 to the cloth or the like becomes easy and a transfer accuracy can be improved.

As described above, when the device transfer sheet according to the embodiment of the present invention is used, the electronic component to which the wirings are connected can be easily transferred to the cloth and a short circuit of the wirings can be prevented.

Also, when only the unnecessary portions are cut in half while the temporary support is left, handling properties of the device transfer sheet can be improved, and it is possible to ensure air permeability, lightweight characteristics, and flexibility of the textile type device after the transfer.

(Method for Producing Device Transfer Sheet and Textile Type Device)

A method for producing a device transfer sheet includes a step of forming wirings on an extensible film to prepare a wiring film, a step of preparing a sensor-attached film having a sensor formed on a temporary support with a protective layer therebetween, and a step of adhering the wiring film to the sensor-attached film such that the wirings and the sensor are connected. Here, the sensor is used as an example of an electronic component.

First, a wiring film is prepared. For example, when a conductive thread is used as a wiring, the conductive thread is sewn into an extensible film. Since the extensible film is thin, the extensible film is very easily torn, but a thin needle and a conductive thread having a small frictional force are used so that breakage of the extensible film can be prevented. Embroidering machines, sewing machines, or the like may be used for sewing or manual sewing may be used. The same applies to a case in which a metallic wire is used.

Also, when a conductive ink is used, the same applies to a case in which the conductive ink is applied to an outer surface.

The wirings are formed such that at least a part thereof is exposed from one surface of the wiring layer. When a conductive thread is used, the conductive thread is exposed on at least one surface of the wiring layer if the conductive thread is sewn to pass through both surfaces of the extensible film. Furthermore, when the conductive thread is exposed only on one side, blindstitching or the like may be used. Blindstitching is a sewing method in which a needle inserted from one side passes through an inside of a film and is pulled from a surface on the side on which the needle is inserted.

Subsequently, the short-circuit prevention layer is provided on a surface of the wiring layer opposite to a surface thereof adhered to the sensor if necessary. The short-circuit prevention layer can be formed on one surface of the extensible film with a thermoplastic film or the like which is thermally melted therbetween.

The sensor-attached film is prepared separately from the preparation of the wiring film. There is no particular limitation on a method for preparing a sensor-attached film. For example, the sensor-attached film can be obtained by sequentially stacking the protective layer and the sensor above the temporary support. To be specific, for example, a commercially available PET film can be used as the temporary support. Moreover, the protective layer is formed above one surface of the PET film. For example, the protective layer may be formed by printing a polyurethane resin or sticking a commercially available polyurethane film thereon. A sensor using ink can be prepared using screen printing at a predetermined position on the obtained protective layer. With such a procedure, the sensor-attached film can be obtained.

Subsequently, the obtained wiring film and the sensor-attached film are adhered. The adhesion is performed such that the wirings and the sensor are electrically connected. At this time, an adhesive layer is formed on at least one of the adhesive surfaces of the wiring film and the sensor-attached film. For this reason, the surface from which the wirings of the wiring film are exposed and the surface on which the sensor of the sensor-attached film is formed is aligned, are subjected to heat application, and are adhered. With such a procedure, the device transfer sheet can be obtained.

Here, in the obtained device transfer sheet, the protective layer and the extensible film constituting the wiring film are formed on the entire surface of the device transfer sheet. Thus, it is desirable to remove the protective layer and the extensible film constituting the wiring film other than a portion along the sensor and the wirings constituting the wiring film such that the temporary support remains. The sensor and the wirings constituting the wiring film are supported by the temporary support even if unnecessary portions are removed.

As described above, the device transfer sheet can be easily produced without complicated steps. For this reason, mass production can also be improved.

Next, the textile type device is produced using the obtained device transfer sheet. A method for manufacturing the textile type device includes a step of adhering the device transfer sheet to the cloth and a step of detaching the temporary support from the adhered device transfer sheet.

An outermost surface of the device transfer sheet opposite to a surface on which the temporary support is provided is an adhesive surface. For this reason, the device transfer sheet is positioned and heated at a predetermined position on the cloth and thus the cloth and the device transfer sheet are fused and joined. In the device transfer sheet, the sensor, the wirings, and the like are already provided in a predetermined arrangement. For this reason, the device can be transferred to a desired position simply through adhesion. Furthermore, since support is performed by the temporary support, the shape does not change significantly at the time of adhering and the accuracy of transfer can be improved.

The temporary support is detached from the device transfer sheet. With such a procedure, the textile type device can be easily obtained.

As described above, the textile type device can be produced in a necessary portion simply by transfer using the device transfer sheet. Furthermore, since the device transfer sheet has stretchability, flexibility, and stability, the accuracy of the positioning can be improved and the resolution of data can be further improved.

REFERENCE SIGNS LIST 100, 101, 102, 103 Textile type device
10 Wiring film
11 Wirings 12 Extensible film
12A, 12C, 12E Adhesive layer
12B, 12D Insulating layer
13 Wiring layer
15 Adhesive film
15A, 15C, 15F Adhesive layer
15B, 15D Insulating layer
20 Sensor
21 Protective layer
30 Circuit board
40 External output means
50 Cloth
60 Temporary support
200 Device transfer sheet

What is claimed is:

1. A wiring film provided between a cloth and an electronic component, the wiring film comprising:
    a wiring layer comprising an extensible film and wirings provided along the extensible film inside and on an outer surface of the extensible film, and
    an adhesive layer on a second surface, which is opposite to a first surface, of the wiring layer,
    wherein at least a part of the wirings is exposed from the first surface of the wiring layer that faces the electronic component,
    the extensible film includes a polyurethane film,
    a thickness of the extensible film is 5 μm to 300 μm, and
    the wirings are not exposed from an outer surface, which is opposite to the first surface, of the adhesive layer.

2. The wiring film according to claim 1, wherein the wirings are a conductive thread or a conductive thread coated with an insulating material.

3. The wiring film according to claim 1, wherein the wirings are a conductive wire or a conductive wire coated with an insulating material.

4. The wiring film according to claim 1, wherein the extensible film comprises a thermoplastic adhesive layer.

5. The wiring film according to claim 1, further comprising:
    a short-circuit prevention layer on the second surface, which is opposite to the first surface, of the wiring layer.

6. The wiring film according to claim 5, comprising:
    a thermoplastic adhesive layer on a surface, which faces the cloth, of the short-circuit prevention layer.

7. A device transfer sheet, comprising:
    the wiring film according to claim 1;
    an electronic component which is connected via an exposed portion of the wirings;
    a protective layer which is configured to cover the wiring film and the electronic component in a plan view; and
    a temporary support which is provided on a surface, which is opposite to a surface of the wiring film side, of the protective layer.

8. The device transfer sheet according to claim 7, wherein the electronic component is a sensor.

9. The device transfer sheet according to claim 7, wherein the protective layer and the wiring film are provided only in a portion along the electronic component and wirings which constitutes the wiring film in the plan view.

10. A textile type device, comprising:
    a cloth;
    the wiring film according to claim 1 adhered on the cloth;
    an electronic component which is connected via an exposed portion of the wirings; and
    a protective layer which is configured to cover the wiring film and the electronic component in the plan view.

11. The textile type device according to claim 10, wherein the protective layer and the wiring film are provided only in the electronic component and the wirings which constitute the wiring film in the plan view.

12. The wiring film according to claim 1, wherein the thickness of the extensible film is 10 μm to 100 μm.

13. The wiring film according to claim 1, wherein the extensible film includes an adhesive layer and an insulating layer from the first surface side of the extensible film.

* * * * *